US009155826B2

(12) United States Patent
Ross et al.

(10) Patent No.: US 9,155,826 B2
(45) Date of Patent: Oct. 13, 2015

(54) METHOD FOR USING PHOTOPLETHYSMOGRAPHY TO OPTIMIZE FLUID REMOVAL DURING RENAL REPLACEMENT THERAPY BY HEMODIALYSIS OR HEMOFILTRATION

(75) Inventors: Edward Allan Ross, Gainesville, FL (US); Richard J. Melker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1317 days.

(21) Appl. No.: 12/985,435

(22) Filed: Jan. 6, 2011

(65) Prior Publication Data

US 2011/0098545 A1    Apr. 28, 2011

Related U.S. Application Data

(62) Division of application No. 11/532,251, filed on Sep. 15, 2006, now Pat. No. 7,887,502.

(51) Int. Cl.
*A61M 37/00* (2006.01)
*A61B 5/00* (2006.01)
*A61M 1/34* (2006.01)
*A61B 5/02* (2006.01)
*A61B 5/026* (2006.01)
*A61B 5/0295* (2006.01)
*A61M 1/36* (2006.01)
(Continued)

(52) U.S. Cl.
CPC .............. *A61M 1/34* (2013.01); *A61B 5/02007* (2013.01); *A61B 5/0261* (2013.01); *A61B 5/0295* (2013.01); *A61B 5/6819* (2013.01); *A61M 1/3609* (2014.02)

(58) Field of Classification Search
CPC .......... A61M 37/00; A61M 5/00; A61B 1/00; A61B 5/00; A61B 5/04
USPC ............................................ 604/5.04, 6.11, 9
See application file for complete search history.

(56) References Cited

U.S. PATENT DOCUMENTS 4,466,804 A    8/1984  Hino
4,710,164 A   12/1987  Leven et al.
(Continued)

FOREIGN PATENT DOCUMENTS

EP         0311709         4/1989

OTHER PUBLICATIONS

Reddan, DN, Szczech LA, Hasselblad V., Lowrie EG, Lindsay RM, Himmelfarb J., Toto RD, Stivelman J., Winchester JF, Zillman LA, Califf RM, Owen WF Jr. Intradialytic Blood Volume Monitoring in Ambulatory Hemodialysis Ppatients: A Randomized Trial. Jounnal of the American Society of Nephorology. 2005; 16:2162-9.

*Primary Examiner* — Tatyana Zalukaeva
*Assistant Examiner* — Ilya Treyger
(74) *Attorney, Agent, or Firm* — Thomas | Horstemeyer, LLP

(57) ABSTRACT

Disclosed herein are methods, systems and devices to monitor vascular volume status during renal replacement therapy utilizing at least one oximetry/photoplethysmography sensor. The methods, systems and devices provide an alternative to conventional vascular volume monitoring methods during renal replacement therapy while enabling reliable, non-invasive, and automatic monitoring of vascular volume to avert patient hypotension. The methods, systems and devices may be employed in the context of both inpatient and outpatient dialysis facilities and may also be incorporated into conventional hemodialysis and hemofiltration techniques and equipment.

7 Claims, 11 Drawing Sheets

(51) Int. Cl.
   *A61M 5/00* (2006.01)
   *A61B 1/00* (2006.01)
   *A61B 5/04* (2006.01)

(56) References Cited

U.S. PATENT DOCUMENTS

| | | |
|---|---|---|
| 4,777,960 A | 10/1988 | Berger et al. |
| 5,032,615 A | 7/1991 | Ward et al. |
| 5,273,036 A | 12/1993 | Kronberg |
| 5,346,472 A | 9/1994 | Keshaviah et al. |
| 5,938,938 A | 8/1999 | Bosetto et al. |
| 6,471,872 B2 | 10/2002 | Kitaevich et al. |
| 6,638,478 B1 | 10/2003 | Treu et al. |
| 6,689,083 B1 | 2/2004 | Gelfand et al. |
| 6,706,007 B2 | 3/2004 | Gelfand et al. |
| 6,780,322 B1 | 8/2004 | Bissler et al. |
| 6,821,441 B2 | 11/2004 | Pedrini et al. |
| 2006/0241506 A1 | 10/2006 | Melker et al. |
| 2008/0190430 A1 | 8/2008 | Melker et al. | securing a first photoplethysmography sensor to a central source site of a patient wherein said sensor is configured to generate a photoplethysmography signal stream from said central source site

Evaluating the PCC or said VCC signals, or both, to determine when the blood flow and/or volume status changes

Adjusting the ultrafiltration rate of said renal replacement therapy responsive to the blood flow and/or volume status change

Processing said signal streams received from said first sensor to obtain a separate PCC signal and a separate VCC signal

FIG. 5

“METHOD FOR USING PHOTOPLETHYSMOGRAPHY TO OPTIMIZE FLUID REMOVAL DURING RENAL REPLACEMENT THERAPY BY HEMODIALYSIS OR HEMOFILTRATION”

RELATED APPLICATION

This application is a division of U.S. Ser. No. 11/532,251 filed Sep. 15, 2006, which is incorporated herein by reference in its entirety.

BACKGROUND

1. Field of the Invention

This invention relates to non-invasive methods for monitoring a patient's vascular volume during renal replacement therapy by means of at least one pulse oximetry/photoplethysmography sensors. Further, this invention relates to monitoring a patient's vascular volume, vascular tone, and/or regional blood flow (e.g. carotid blood flow as a surrogate for cerebral blood flow) during renal replacement therapy using photoplethysmography methods and adjusting the rate of ultrafiltration real-time during the patient's treatment.

2. Discussion of the Art

Renal Replacement Therapy (RRT) has evolved from the long, slow hemodialysis treatment regime of the 1960's to a diverse set of therapy options, the vast majority of which employ high permeability membrane devices and ultrafiltration control systems.

Biologic kidneys remove metabolic waste products, other toxins, and excess water. They also maintain electrolyte balance and produce several hormones for a human or other mammalian body. An artificial kidney, also called a hemodialyzer or dialyzer, and attendant equipment and supplies are designed to replace the blood-cleansing functions of the biologic kidney. At the center of artificial kidney design is a semipermeable filter membrane that allows passage of water, electrolytes, and solute toxins to be removed from the blood. The membrane retains in the blood, the blood cells, plasma proteins and other larger elements of the blood.

Over the last 15 years, the intended use of the RRT has evolved into a subset of treatment alternatives that are tailored to individual patient needs. They include ultrafiltration, hemodialysis, hemofiltration, and hemodiafiltration, all of which are delivered in a renal care environment, as well as hemoconcentration, which is typically delivered in open heart surgery. Renal replacement therapies may be performed either intermittently or continuously, in the acute or chronic renal setting, depending on the individual patient's needs.

Ultrafiltration involves the removal of excess fluid from the patient's blood by employing a pressure gradient across a semipermeable membrane of a high permeability hemofilter or dialyzer. For example, removal of excess fluid occurs in hemoconcentration at the conclusion of cardiopulmonary bypass surgery. Hemodialysis involves the removal of toxins from the patient's blood by employing diffusive transport through the semipermeable membrane, and requires an electrolyte solution (dialysate) flowing on the opposite side of the membrane to create a concentration gradient. A goal of dialysis is the removal of waste, toxic substances, and/or excess water from the patients' blood. Dialysis patients require removal of excess water from their blood because they lack the ability to rid their bodies of fluid through normal kidney function.

One of the potential risks to health associated with RRT is hypotension, which is an abnormal decrease in the patient's blood pressure. An abnormally high or uncontrolled ultrafiltration rate may result in hypovolemic shock, hypotension, or both. If too much water is removed from the patient's vascular compartment, such as might occur if the ultrafiltration rate is too high or uncontrolled, the patient could suffer hypotension and/or go into hypovolemic shock. Accordingly, RRT treatments must be controlled to prevent hypotension.

Rapid reduction in plasma or blood volume due to excessive ultrafiltration of water from blood may cause a patient to exhibit one or more of the following symptoms: hypovolemia-hypotension, diaphoresis, cramps, nausea, or vomiting. During treatment, vascular volume in the patient's blood would theoretically remain constant if the plasma refilling rate equaled the ultrafiltration rate. However, refilling of the plasma is often not completed during a RRT session. The delay in refilling the plasma can lead to insufficient blood volume in a patient.

There appears to be a "critical" blood volume value below which patients begin to have problems associated with hypovolemia (abnormally decreased blood volume). Fluid replenishing rate is the rate at which the fluid (water and electrolytes) can be recruited from tissue into the blood stream across permeable walls of capillaries. This way blood volume is maintained relatively constant. Most of patients can recruit fluid at the rate of 500 to 1000 mL/hour. When patients are treated at a faster fluid removal rate, they begin to experience symptomatic hypotension. A mismatch occurs when the ultrafiltration rate exceeds the plasma refilling rate. Typically, vascular tone, a compensatory mechanism, increases to offset this mismatch but not all individuals have a functioning compensatory mechanism.

Hypotension is the manifestation of hypovolemia or a severe fluid imbalance, especially when there is a failure to activate compensatory mechanisms, such as individuals with anatomical neuropathy who lack responsive vascular tone. Symptomatically, hypotension may be experienced by the patient first as light-headedness. To monitor patients for hypotension, non-invasive blood pressure monitors are commonly used during RRT. When detected early, hypotension resulting from the excessive loss of fluid is easily reversed by giving the patient intravenous fluids. Following administering fluids the RRT operator can adjust the ultrafiltration rate to make the RRT treatment less aggressive.

Ultrafiltration controllers were developed specifically to reduce the occurrence of hypotension in dialysis patients. Ultrafiltration controllers can be based on approximation from the known trans-membrane pressure, volume based or gravity based. Roller pumps and weight scales are used in the latter to meter fluids. Ultrafiltration controllers ensure the rate of fluid removal from a patient's blood is close to the fluid removal setting that was selected by the operator. However, these controllers do not always protect the patient from hypotension. For example, the operator may set the fluid removal rate too high. If the operator setting is higher than the patient's fluid replenishing rate, the operator should reduce the rate setting when the signs of hypotension manifest. If the excessive rate is not reduced, the patient may still suffer from hypotension, even while the controller operates properly. Reddan D N, Szczech L A, Hasselblad V, Lowrie E G, Lindsay R M, Himmelfarb J, Toto R D, Stivelman J, Winchester J F, Zillman L A, Califf R M, Owen W F Jr. Intradialytic Blood Volume Monitoring in Ambulatory Hemodialysis patients: A Randomized Trial. Journal of the American Society of Nephrology. 2005; 16:2162-9

Attempts were made during the last two decades to develop monitors that could be used for feedback control of dialysis machine parameters, such as dialysate concentration, temperature, and ultrafiltration rate and ultrafiltrate volume. Blood volume feedback signals have been proposed that are based on optical measurements of hematocrit, blood viscosity and blood conductivity (impedance). Real-time control devices have been proposed that adjust the ultrafiltration rate to maintain a constant blood volume, and thereby balance the fluid removal and fluid recruitment rates. None of these proposed designs led to significant commercialization owing to the high cost of sensors, high signal to noise ratio or lack of economic incentive for manufacturers. In addition, many of these proposed systems required monitoring of patients by highly trained personnel.

The danger of hypotension as a consequence of excessive fluid removal during dialysis and other extracorporeal blood treatments has been recognized. U.S. Pat. No. 5,346,472 describes a control system to prevent hypotension that automatically adjusts the sodium concentration added to the dialysate by infusing a hypertonic or isotonic saline solution in response to operator input or patient's request based on symptoms. European patent EU 0311709 to Levin and Zasuwa describes automatic ultrafiltration feedback based on arterial blood pressure and heart rate. U.S. Pat. No. 4,710,164 describes an automatic ultrafiltration feedback device based on arterial blood pressure and heart rate. U.S. Pat. No. 4,466,804 describes an extracorporeal circulation system with a blood oxygenator that manipulates the withdrawal of blood to maintain CVP constant. U.S. Pat. No. 5,938,938 describes an automatic dialysis machine that controls ultrafiltration rate based on weight loss or the calculated blood volume change. Late model AK200 dialysis machines from Gambro (Sweden) include an optional blood volume monitor called BVS or Blood Volume Sensor. This sensor is optical and in fact measures blood hematocrit, or the concentration of red blood cells, in blood. Since dialysis filter membranes are impermeable to blood cells, increased hematocrit signifies the reduction of the overall blood volume. The BVS sensor is included in a feedback to the machine and is used to help the operator assess the rate of fluid removal. However, as realized by the inventors, this and similar technology have failed to show clinical relevance due to failure to measure compensatory mechanisms and importance of regional (e.g. cerebral) blood flow.

More recent references have further focused on the danger of hypotension as a consequence of excessive fluid removal during dialysis and other extracorporeal blood treatments. U.S. Pat. No. 6,821,441 describes a method for blood purification by means of hemodialysis and/or hemofiltration wherein a blood parameter selected from trans-membrane pressure, hematocrit value and blood density is monitored to control the infusion rate of a substitution fluid into a patient's blood. U.S. Pat. No. 6,706,007 describes a system that non-invasively monitors blood oxygen levels to detect when hypotension is about to occur in a patient undergoing extracorporeal treatment of their blood. U.S. Pat. No. 6,689,083 describes a system that non-invasively monitors osmotic pressure across a filter membrane of a blood filter to detect when hypotension is about to occur in a patient undergoing extracorporeal treatment of their blood.

SUMMARY

In one regard, superior RRT monitoring methods would be able to provide real-time continuous measurements of signals that would be analyzed to provide relative blood flow and/or volume, blood pressure, and pulse rate. Such superior RRT monitor systems would utilize pulse oximetry/photoplethysmography at a highly perfused central tissue site, such as the lip, tongue, nares, cheek. Optionally, a second additional may be located at a typically less perfused area such as a finger or toe. It is desired to have such superior monitoring methods, which are more reliable, are capable of averting patient hypotension, allow cross-site comparisons of blood flow and/or volume and provide non-invasive feedback based control methods that continuously and automatically manipulate the ultrafiltration rate to achieve an optimal ultrafiltration rate.

Methods, systems and devices have been developed for optimizing fluid removal during renal replacement therapy (RRT) in which the ultrafiltration rate is adjusted in real-time during a patient's treatment and further not requiring human monitoring and/or interaction. The present invention senses a fall in carotid blood flow or failure of compensatory mechanisms resulting in cerebral hypoperfusion. By monitoring blood flow and/or volume status, via photoplethysmography, the system detects a decrease of central blood volume that precedes the onset of hypotension and maintains a safe filtration rate by reducing the ultrafiltration rate when the blood flow and/or volume status feedback signal decreases, indicating that hypotension may occur. Adjustment of the ultrafiltration rate may be manually performed by the healthcare practitioner or adjustment may be automated using a real-time blood flow and/or volume status feedback signal, thereby averting hypotension before it occurs.

The present invention provides a method of optimizing fluid removal during renal replacement therapy, said method comprising securing a pulse oximeter/photoplethysmography probe to a central source site of a patient wherein said probe is configured to generate a signal stream indicative of blood flow and/or volume status at said central source site; processing said signal stream received from said probe to obtain a separate pulsatile cardiac component (PCC) signal and venous capacitance component (VCC) signal; evaluating said PCC signal, or VCC signal, or both, to determine the occurrence of a change in blood flow and/or volume status; and adjusting the ultrafiltration rate of said patient's renal replacement therapy responsive to said change in blood flow status. The method allows for the comfortable and non-invasive monitoring of a patient's blood flow and/or volume status during renal replacement therapy and further provides optimization of the ultrafiltration rate capable of averting hypotension. This invention also measures compensatory mechanisms such as vascular tone, which in turn is used as a diagnostic tool to detect deficiencies in such mechanisms.

It is to be understood that the foregoing general description and the following detailed description are exemplary and explanatory only and are not to be viewed as being restrictive of the present, as claimed. These and other objects, features and advantages of the present invention will become apparent after a review of the following detailed description of the disclosed embodiments and the appended claims. All patents, patent applications and publications discussed or cited herein are incorporated by reference to the same extent as if each individual publication or patent application was specifically and individually set forth in its entirety.

BRIEF DESCRIPTION OF THE DRAWINGS

FIG. 5 shows a diagram representing a method for optimizing fluid removal during renal replacement therapy that employs photoplethysmography signals obtained from the patient.

DETAILED DESCRIPTION

Figure 1:
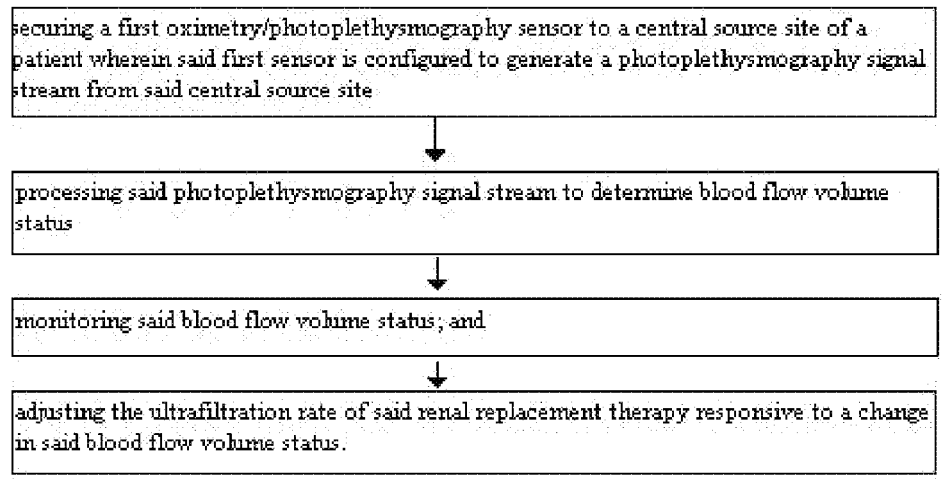
FIG. 1 shows a diagram representing a method for optimizing fluid removal during renal replacement therapy that employs photoplethysmography signals obtained from the patient.

Some embodiments of the present invention are directed to methods that utilize a pulse oximeter/photoplethysmography sensor to optimize fluid removal during renal replacement therapy (RRT). To the inventors' knowledge, no one has previously thought of using photoplethysmography for such purpose. Embodiments also pertain to measuring a patient's vascular volume, vascular tone, and/or regional blood flow (e.g. carotid blood flow as a surrogate for cerebral blood flow).

Traditionally, a photoplethysmography signal stream is typically obtained from a peripheral site such as the finger, or other extremity, which is usually damped and difficult to process and therefore to interpret. The inventors have discovered that obtaining the photoplethysmograph from a central source site (CSS) eliminates much of the background noise and poor signal to noise ratio found in the plethysmograph from a peripheral source site (PSS), and it is the obtention of this "less noisy" signal that eventually led to the realization that information such as respiration rate, pulsatile carotid blood flow, and venous capacitance can be extrapolated, as well as carotid blood flow as a surrogate for cerebral blood flow. Additionally, collection of at least two photoplethysmography signal streams, one from a CSS site and one from a PSS, enhances the reliability and accuracy of the methods disclosed to monitor a patient's blood flow and/or volume status during RRT, thereby averting hypotension.

Typically, photoplethysmography is conducted using one pulse oximeter probe. The raw signal stream obtained from a pulse oximeter probe is related to the amount of light from the LED that hits the photodetector of the pulse oximeter probe. The magnitude of the signal from the photodetector is inversely proportional to the amount of absorption of the light between the LED and the photodetector (greater absorption results in less light exciting the photodetector). The absorbed light is due to multiple factors, including absorption due to tissue, absorption due to venous blood, absorption due to arterial blood, and absorption due to the pulsation of arterial blood with each heart beat. As previously characterized (WO-A 2006086010), three separate components of the plethysmograph signal have been discovered: (a) PCC, (b) low frequency venous capacitance component (VCC), and (c) the classical DC component signal which is a function of the tissue (muscle, bone, etc) at the probe site, and is the baseline DC component on which the venous capacitance signal rides. The raw plethysmograph signal can be processed to separately identify such components. Thus, the PCC component pertains to a component of a processed plethysmographic signal that represents the pulsatile blood flow that is present in the vascular bed being monitored. The VCC component pertains to a phasic slower frequency signal that represents the venous capacitance of blood in the vascular bed being monitored and is influenced by variations in intrathoracic pressure and venous blood volume.

One embodiment for isolating the PCC and the VCC comprises:
1) discretely selecting the peaks and troughs of the signal (improved noise/artifact rejection can be achieved by looking for peaks and troughs that exist at the expected heart rate, estimated by Fourier or autocorrelation analysis, or from past good data)
2) finding the midpoints (or minimum values) between peaks and troughs
3) extracting the VCC as the interpolated (and possibly smoothed or splined) line that connects these midpoints (or minimum values)
4) extracting the PCC as the raw signal subtracted from the VCC; and optionally
5) includes magnitude of the pulsation.

This processing is preferably implemented from signals obtained from a central source site, but it could be applied to signals obtained from other sites so long as the fidelity of the signal is sufficiently high and reliable. This technique achieves a nonlinear filter with zero delay and optimally separates the two signals of interest. In view of the teachings herein, those skilled in the art will appreciate that similar techniques for achieving these objectives could also be adapted, and are differentiated from the conventional processing of plethysmography signals due to their goal of optimally separating the two signals of interest on a beat-to-beat, zero delay basis (unlike standard linear filtering, DC removal techniques, and averaging techniques).

The amplitude and area under the curve (AUC) of the AC component contains information about the amount of arterial blood flowing past the detector. In order to correctly interpret this information, the PCC and VCC components must be separated more rigorously than with the algorithms in standard monitors and previously described in the literature. In particular, the PCC should contain only that information that relates to beat-to-beat variations of the heart. The VCC component should contain lower frequency effects from physiology (such as the respiratory effects, blood pooling, venous capacitance, etc.) and physical sensor changes (e.g. changes in the orientation of the probe, etc.).

Pulse oximeter probes useful in accordance with the teachings herein include, but are not limited to, those described in U.S. Pat. Nos. 7,024,235; and 6,909,912 and co-pending U.S. application Ser. Nos. 10/751,308; and 60/600,548, the disclosures of which are all incorporated herein in their entirety.

Typically, the probes comprise an LED that emits its specific frequency hundreds of times per second, and the absorption (or transmittance) readings by a sensor, such as a photodiode, are transmitted to a computer. There a software system performs averaging (optionally deleting outliers), and by differences in wavelengths' absorption or transmittance at the pulse peaks, determines arterial oxygen saturation. In a standard two-LED system, this is done by an algorithm that calculates the ratio of the peak absorbance at 650-670 nm divided by the base absorbance at this wavelength range, and compares this ratio to the peak absorbance at 880-940 nm to the base absorbance at the 880-940 nm range. The base absorbance reflects the non-pulse background absorbance by tissues other than the artery at maximum width during the pulse. This calculation provides an estimate of arterial oxygen saturation. A graph of the pulse waveform, or shape, over time, also can be obtained.

As referred to above, the VCC of the photoplethysmograph is an indicator of venous capacitance, while the PCC is a measure of regional blood flow. Previously described is the discovery that both PCC and VCC components to be useful in monitoring both normal and abnormal respiration events. During forced airway maneuvers, intrathoracic pressure changes dramatically. These pressure changes are transmitted directly to the veins in the head, because there are no anatomical valves in veins leading to the head. Changes in intrathoracic pressure have direct effects on both the beat to beat PCC, and the amount of venous blood in the vascular bed being monitored on a breath to breath basis. These effects are present even during quiet breathing, but are far more pronounced with "airway maneuvers" such as the Valsalva and Mueller maneuvers, and during exacerbation of respiratory conditions which increase airway resistance and/or decrease lung compliance. These pronounced changes are often referred to as "pulsus paradoxus" when measured by arterial blood pressure or direct arterial blood monitoring. All conditions which affect airway resistance (increase) and lung compliance (decreased) increase the respiratory muscle work (work of breathing for each breath, or power of breathing for the amount of total work performed in one minute). As the work or power of breathing increases, there are wider swings in intrathoracic pressure which in turn lead to phasic variations in pulsatile cardiac blood flow and venous capacitance. Respiratory rate can be determined when monitoring at "central source sites" and the degree of change in both the PCC and VCC components are proportional to the degree of airway obstruction and/or lung compliance. At a given level of resistance and or compliance, variations in the amplitude and AUC of both components can also be an indication of volume status. Thus, a plethora of information on both respiratory and cardiopulmonary mechanics can be ascertained from the processed plethysmograph, especially when it is obtained from a "central source site". As will be described herein, this knowledge can be implemented to assist in determining physiological changes associated with hemodialysis.

The present invention provides a novel means of utilizing cardiopulmonary information from a processed plethysmograph, specifically the PCC and VCC components, to optimize fluid removal rates, monitoring vascular tone, and/or regional blood flow in patients undergoing RRT. Algorithms to evaluate the PCC and VCC include, but are not limited to, separating the high frequency information in the PCC (heart rate and above, typically above 0.75 Hz) information, the low frequency information in the VCC (e.g. respiratory rate and changes in blood volume, typically from 0.05 Hz to 0.75 Hz) and the very low frequency information in the DC offset (e.g. changes in pulse oximeter path length (positioning), typically less than 0.05 Hz). Separating these waveforms without delays or significant averaging is required to optimally extract information from the photoplethysmograph (PPG,). The PPG typically has only 3-5 heart beats (the major feature of the signal) for each breath (the second largest signal). If significant averaging or delays exist, the secondary signal (VCC) cannot be reliably separated from the primary signal (PCC). Other methods exist that can be utilized to extract these signals. Wavelets allow for finer resolution at low frequencies than the more standard Fourier spectral analysis methods. Adaptive filtering may also be used to optimally adjust the cutoff frequency between the breathing rate and heart rate. If coarse information is all that is required, many standard methods can be used to separate the signals, including linear filtering, frequency domain filtering, time domain analysis such as zero-crossings and moving averages, nonlinear filtering, modeling such as Kalman filtering and ARMA modeling, and other methods known to those skilled in the art.

Quantification of the PCC and VCC changes can include peak or trough counting, peak-peak timing, peak-trough height, area under the curve, shape of the curves, frequency characteristics of the curves, entropy of the curves, changes in the positions of the peaks, troughs, or midpoints from heart beat to heart beat or breath to breath. Some of these parameters may need to be normalized by the LED signal power, DC offset, or the physiology of the probe placement.

The term "central source site" as used herein refers to a site at or above the patient's neck. Particularly preferred central source sites, include, but are not limited to, a patient's nasal septum, nasal alar, pre-auricular region, post auricular region, tongue, forehead, lip, or cheek, ear canal, or combinations thereof.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information. A computer, as used herein, is a device that comprises at least one processing module.

As will be appreciated by one of skill in the art, embodiments of the present invention may be embodied as a device, method, or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Embodiments of the present invention utilize the PCC to monitor a patient's blood volume status, monitoring vascular tone and/or regional blood flow during renal replacement therapy. Once the signal components are separated, variations in the amplitude and AUC of both the PCC and VCC components can be indicative of a change in blood flow and/or volume status.

One aspect of the present invention relates to a novel method of non-invasively monitoring blood flow and/or volume status using at least one pulse oximeter/photoplethysmography probe positioned on the body of a patient, the signal from which may be capable of indicating a decrease in a patient's blood flow and/or volume, wherein decreasing blood volume may lead to hypotension. In practice a probe emits at least two different light frequencies, such as by light-generating diodes (LEDs), and such emitted light is detected by at least one light detector, such as a photodiode detector. A general-purpose computer or a special purpose computer is employed to perform complex mathematical computations based, typically, on the signal intensity and timing from the at least one pulse oximeter probe, and on signals from the light detectors of each probe. Proper analysis by software programming in such general-purpose computer or special purpose computer outputs results to a display, printer, etc. that suggests or indicates (depending on relative differences in the signal, and upon other conditions) whether blood flow and/or volume has changed in a selected body area.

In one embodiment, prior to RRT, the amplitude and area under the curve (AUC) of the PCC component of the CSS and the PSS plethysmographs would be measured. A ratio of the amplitudes and/or the AUC is then calculated, representing the relative blood flow to the head (brain) and the PSS (finger, toes). In humans with normal compensatory mechanisms, this ratio will change (i.e. greater flow to the head than finger) during acute fluid loss (hypovolemia) as the body shunts blood to the brain at the expense of the peripheral circulation. If peripheral flow is the numerator of the ratio and central flow the denominator, then the ratio will decrease with increasing fluid loss. Initially, the PSS amplitude/AUC will decline, but the CSS amplitude/AUC will remain unchanged. With continued loss, both will decline, but PSS will decline further. At some point, peripheral flow will essentially cease and central flow will continue to decline. This reversal in the ratio, in the absence of volume resuscitation, would be an ominous sign.

Similar changes in this ratio should be seen in dialysis patients with intact compensatory mechanisms. However since many dialysis patients lose these normal reflexive responses to fluid depletion, the distribution of blood flow between the central and peripheral sites is abnormal and therefore unpredictable. Without normal compensatory mechanisms, blood flow to both the PSS and CSS will decline and the ratio may remain unchanged in the face of significant volume loss. Measurement of this ratio will be a good predictor of how well dialysis patients will tolerate dialysis.

When two or more probes are used together, data from multiple probes is processed to provide continuous and simultaneous cross-site comparisons of the blood flow and/or volume status between two or more tissue sites (and, as desired, blood pressure estimates based on transit time differences and/or other related parameters). The monitoring system receiving these signals includes at least one program containing computer software (not shown) comprising instructions which causes the computer processor to receive and calculate various blood flow and/or volume values. Optionally, the monitoring system may receive signals from separate probes or sensors to assess blood pressure values, which optionally may be compared (either simultaneously or separately) with blood pressure estimates based on signals received from each of the probes determining blood flow and/or volume of a patient.

In a specific embodiment, a monitoring device is provided having different function modes, such as a calibration mode and a monitoring mode to assist in this process. During the calibration mode, the device is calibrated to obtain PCC and VCC component values during normal blood flow and/or volume states (i.e. non-RRT time periods). These values are stored in the device. When undergoing RRT, the patient is monitored with the device in a monitoring mode. During monitoring mode, the PCC and/or VCC values are observed and compared to those obtained during calibration mode. The device preferably has a readout screen to display information, and is preferably configured to display the variance in blood flow and/or volume. This device and methodology may be implemented to monitor the blood flow and/or volume for different medical conditions.

The apparatuses, methods and systems of the present invention can be applied to both humans and animals, i.e., to living vertebrate organisms. Its application in human medicine (adult & pediatrics) would significantly improve the estimation of blood flow and/or volume status by pulse oximetry/photoplethysmography; however, veterinary medicine also would greatly benefit from its use. This superior monitoring system would utilize at least one pulse oximeter probe, which is designed for use with a highly perfused central tissue, such as a lip, tongue, nares, cheek.

As discussed in further detail in Example 5 below, it has been discovered that certain patient populations (such as diabetic or kidney failure patients) exhibit compromised compensatory mechanisms (e.g. attenuated increase in vascular tone compared to normal populations upon removal of fluid). It was revealed that "healthy" patients showed a significant decrease in the amplitude of the photoplethysmgraph pulse obtained at the nasal alar, whereas the susceptible patients showed little change in the amplitude of the pulse. It was realized that the change in amplitude by the healthy patients was due to a normal contraction of the vasculature so as to maintain an appropriate blood pressure and blood flow to a person's brain. Normally, the amplitude of the pulsation decreases as vascular tone increases and the blood vessel wall becomes less compliant. In contrast, the compromised patients (e.g. with diabetes, autonomic neuropathy, kidney failure) show little drop in the amplitude, which is due to their attenuated vascular tone responses. Based on discovering this relationship between the change/or absence of change in the amplitude of the pulse and compensatory mechanisms, the strength of a patient's compensatory mechanisms can be determined. This will assist in determining potential risks and predicting abnormal responses that a patient may exhibit as a result of fluid and/or blood loss. Accordingly, another embodiment of the invention comprises a method of evaluating the magnitude of a patient's compensatory mechanisms (those mechanisms such as increased vascular tone which act to maintain blood pressure upon loss of fluid/blood) which comprises perturbing a patient's vascular system and monitoring the amplitude of a photoplethysmography signal stream from a central source site of said patient. In addition, a grading system for the strength of the compensatory system can be devised based on the degree of change in the amplitude of the signal. Perturbing the system can be achieved by non-invasive means such as maneuvering a patient so as to be subject to gravity in a vertical (upright) direction. For example, this may include, but is not limited to, having a patient quickly standing up from a prone, supine or sitting position. Gravity simulators could also be implemented. Perturbing the vascular system may occur by invasive means such as by removing fluid or blood from the patient (e.g. during hemodialysis or other extracorporeal therapies). Invasive means can occur during surgery which will help predict the degree by which fluid or blood loss will affect the patient. This information will be very helpful to improve health outcomes during and recovering from surgery. The perturbation of the vascular system might occur due to trauma resulting in blood loss, wherein an emergency response person can quickly assess the capacity of a patient's compensatory mechanisms at the emergency site (car accident, battlefield injury, etc.).

The following specific examples are meant to be demonstrative, but not limiting, of the possible applications of the present invention.

Example 1

FIG. 1 demonstrates a method for optimizing fluid removal in a patient undergoing RRT. A central pulse oximetry/photoplethysmography sensor is placed on the cheek, nasal septum, alar nares, or tongue. An optional peripheral pulse oximetry/photoplethysmography sensor may be placed on the patient's finger or toe. Before and during dialysis, a number of derived parameters are monitored. At the start of dialysis, the amplitude and area under the curve (AUC) of the fast component of the photoplethysmograph are calculated from one or more monitoring sites and a ratio of the amplitudes and/or AUC is calculated. This represents the relative blood flow to the head (brain) and the optional peripheral site. As fluid is removed during RRT, this ratio may change (i.e. greater flow to the head than finger) or since many dialysis patients lose the normal reflexive responses to fluid depletion, there may be an equal or greater loss in amplitude and the AUC from the probes monitoring the head. Additionally, the slow component of the photoplethysmograph would be separated from the fast component. The slow component of the photoplethysmograph closely correlates with venous capacitance and the amplitude and AUC should diminish with fluid withdrawal.

A fall in central blood volume would initiate a decrease in the ultrafiltration rate and refilling of the vascular space would permit reinstitution of fluid removal. Ideally, an electronic feedback circuit would automate this process; however, a manual process could be utilized by the nursing staff. This methodology would also help patients with an unknown amount of excess fluid. Ultrafiltration rates and absolute goals could be adjusted based on when the central blood volume begins to decline. This technology would have great benefits to inpatients who are already hemodynamically unstable, as well as outpatients on hemodialysis.

Example 2

Figure 2:
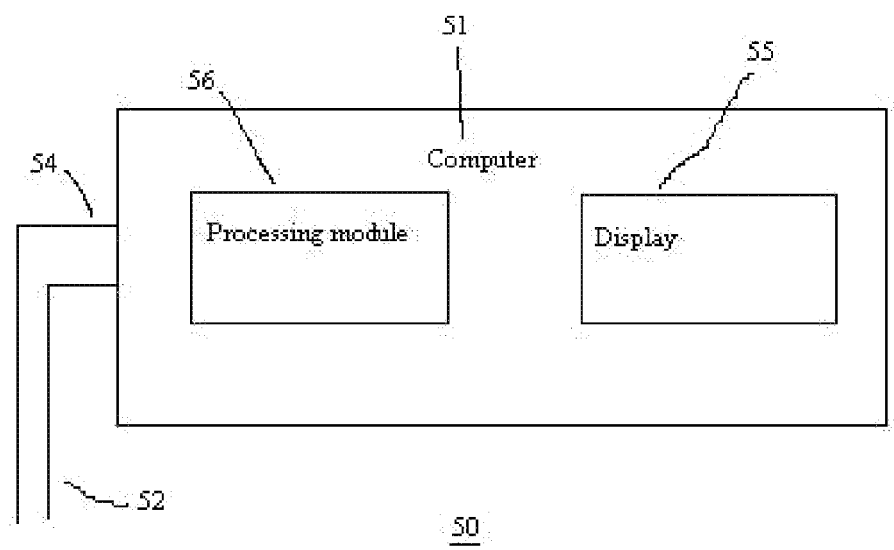
FIG. 2 shows a schematic of a system for optimizing fluid removal during renal replacement therapy that employs photoplethysmography signals obtained from the patient.

In FIG. 2, there is shown a system 50 for obtaining and processing photoplethysmography data from a patient for purposes optimizing fluid removal during RRT to avert hypotension. The system comprises a computer 51 that is configured to receive and process signals from lines 52 and 54, which are distally connected to one or more pulse oximeter probes (not shown) located on the patient. Those skilled in art will appreciate that the signals may be preprocessed to some degree by a separate signal processor and subsequently sent as one signal stream to the computer 51. Thus, the computer 51 is configured to receive signals from either lines 52 or 54 or a combination of both. Typically, one of the lines will carry power from the computer 51 to the pulse oximeter probe, while the other line carries signals back to the computer 51. The computer 51 comprises a processing module 56 with program code module(s) and/or electrical/circuitry components associated therewith to direct the processing of the signal stream from lines 52 and/or 54. The processing module 56 separates out the venous capacitance component from the signal stream as described above. The processing module 56 also comprises a program code module(s) and/or electrical/circuitry components associated therewith to analyze the signal stream to determine blood flow and/or volume status. In a preferred embodiment, the processing module 56, or a separate processing module, is directed to generate a report indicating a patient's blood flow and/or volume status and any changes in the blood flow and/or volume status. Also in a preferred embodiment, the processing module 56, or a separate processing module, is directed to adjust the ultrafiltration rate responsive to a change in the blood flow and/or volume status.

Furthermore, the computer 51 comprises a display 55 showing the signal produced by the pulse oximeter probe as well as displaying information regarding the processing and/or analysis of the data from the patient. Those skilled in the art will appreciate that the display, or other suitable components, may be integral with, attached to or separate from computer 51. The computer may also comprise a control panel with a keyboard, buttons, and/or touchpad to input commands or other information.

Figure 3:
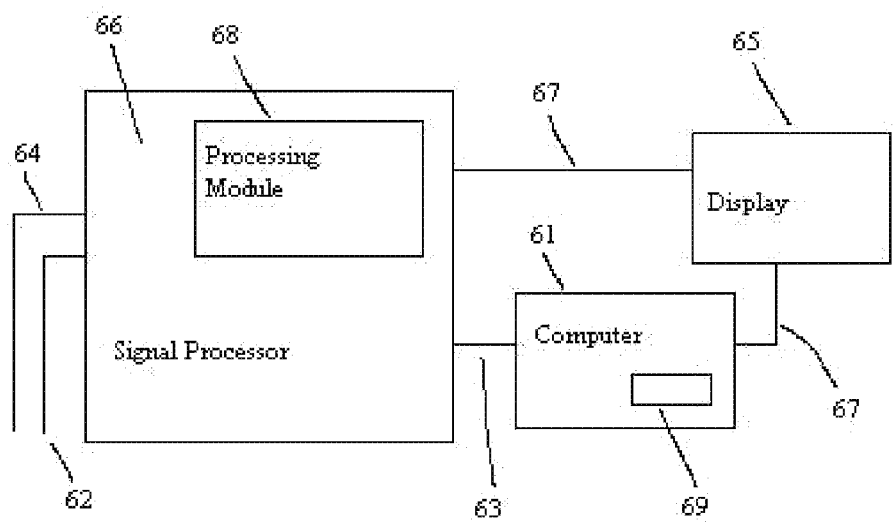
FIG. 3 shows a schematic of a system for optimizing fluid removal during renal replacement therapy that employs photoplethysmography signals obtained from the patient.

FIG. 3 is a representation of a similar system where the components are separated. Those skilled in the art will readily appreciate that two or more components of the system may be combined into a single housing unit or, alternatively, two or more components may be separate but connected through appropriate wires, or wireless communication means. The system 60 comprises a signal processor 66 which is configured to send/receive signals to/from lines 62, 64 which are connected to a pulse oximeter probe (not shown). The signal processor 66 comprises a processing module 68 configured to separate out the PCC and VCC contained in the signal stream received from the pulse oximeter probe. The PCC signal stream and/or the VCC signal stream is sent to a computer 61 through line 63. The computer 61 comprises a processing module 69 to analyze the PCC signal stream and/or VCC signal stream to monitor blood flow and/or volume status. Information generated from the signal process 66 and/or computer 61 may be sent to a display 65 via lines 67.

Example 3

Figure 4:
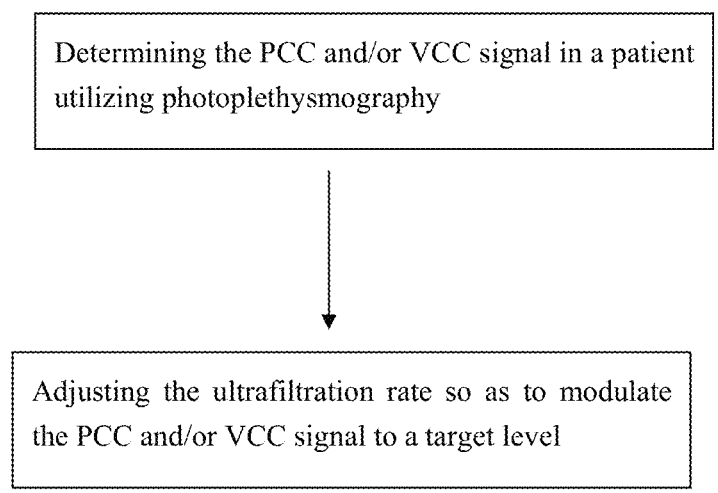
FIG. 4 shows a diagram representing a method for optimizing fluid removal during renal replacement therapy that employs photoplethysmography signals obtained from the patient.

FIG. 4 demonstrates a method for optimizing fluid removal during RRT by use of photoplethysmography to monitor a patient's blood flow and/or volume status. The method comprises determining the arterial component signal and/or the venous capacitance component signal in said patient utilizing photoplethysmography; and adjusting the ultrafiltration rate so as to modulate the arterial component signal and/or the venous capacitance component signal to maintain a patient's blood flow and/or volume status at a target level.

Example 4

FIG. 5 demonstrates a method for optimizing fluid removal during RRT by use of photoplethysmography to monitor a patient's blood flow and/or volume status. The method comprises the steps of securing a first photoplethysmography sensor to a central source site of a patient wherein the sensor is configured to generate a photoplethysmography signal stream from the central source site; processing the signal streams received from the first sensor to obtain a separate arterial component signal and a separate venous capacitance component signal, wherein processing the signal stream information comprises processing photoplethysmography signal information; evaluating the arterial component signal, or the venous capacitance component signal, or both, to determine when the blood flow and/or volume status changes; and adjusting the ultrafiltration rate of the RRT responsive to the blood flow and/or volume status change.

Example 5

Photoplethysmograph (PPG) Monitoring of Carotid Blood Flow Parameters at the Nasal Alar Measures of hemoconcentration during hemodialysis do not reliably predict hypotension, which may be due to impaired compensatory responses to even small fluid removal volumes. The inventors sought to devise new noninvasive photoplethysmograph (PPG) technology for monitoring carotid blood flow parameters at the nasal alar, quantify the cardiac and respiratory components, and study the effect of fluid losses and resistance breathing in dialysis patients and blood donors.

Efforts to develop practical PPG systems to study the effect of fluid losses, and other aspects mentioned in the preceding paragraph, have to date been limited by dampening of the signals at the periphery (e.g. attached to fingers or toes) or inconsistent waveforms at easily traumatized tissue (i.e. nasal septum). To overcome those shortcomings the inventors have developed a comfortable probe that produces stable signals from the highly vascular alar portion of the nose, being supplied by both the external and internal carotid arteries. The inventors have conducted studies in human subjects which have demonstrated that PPG technology can be utilized to monitor certain physiological parameters as discussed above, as well as detect potential risks to patients undergoing RRT, or experiencing some other perturbation to the vascular system involving fluid and or blood loss.

Methods and Materials

The study protocol was approved by the University of Florida Institutional Review Board (Gainesville, Fla.), adhered to all HIPAA privacy requirements, and written consent was obtained from all subjects. The 20 blood donors were recruited after having met the usual inclusion and exclusion criteria for a one unit phlebotomy (LifeSouth Community Blood Centers, Gainesville, Fla.). The 20 hemodialysis patients were undergoing care at the University of Florida & Shands Hospital outpatient dialysis unit. For all subjects the height, weight, age, and seated blood pressures before and after their respective procedures were recorded.

Figure 11:
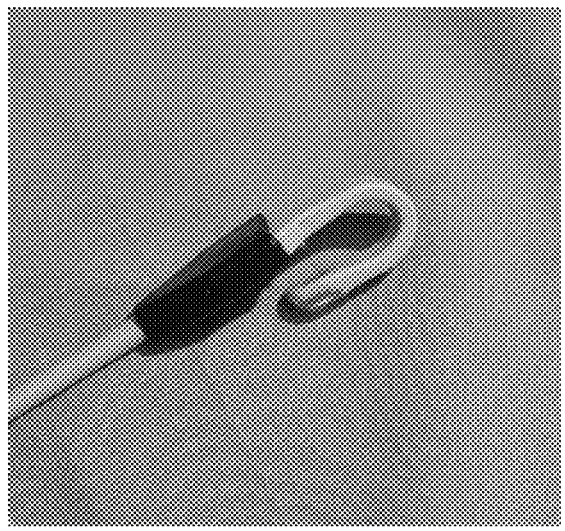
FIG. 11 is a photograph of an exemplary nasal alar probe.

A nasal alar pulse oximeter probe (FIG. 11) was placed on the subjects prior to undergoing their procedure (blood donation or hemodialysis). We utilized a pulse oximeter probe developed jointly with Beta Biomed Services (Rowlett, Tex.). It was connected to a Novametrix Oxypleth 520A pulse oximeter (Respironics Inc, Murrysville, Pa.) and data were collected continuously. Since we hypothesized that intrathoracic pressure would be a key determinant for the PPG signal, we utilized a range of resistance breathing profiles so as to quantify that effect. Subjects were asked to breathe through various sizes of endotracheal tubes that were attached to a mouthpiece, which was connected to a $CO_2$SMO Plus (Novametrix, Respironics Inc.) in-line sensor that measured respiratory air flow and tidal volume. Raw data from the alar probes was recorded and stored on a PC using proprietary software which communicated with the Oxypleth and also recorded and stored the parameters measured by the $CO_2$SMO. All subjects practiced the resistance breathing maneuvers outlined below prior to the start of their blood donation or dialysis. Three endotracheal (ET) tube sizes were used to create resistance: 10.2 cm length with 3.5 mm diameter (high resistance), 10.2 cm length (medium resistance) with 4.0 mm diameter, and 7.6 cm length with 5.5 mm diameter (low resistance). The order in which the subjects breathed through the ET tubes was randomized. Subjects breathed at peak inspiratory and expiratory flow rates of 40 L/min to a volume of 1.5 L per breath. The data collection software included a real-time graphical display of respiratory flow and volume, and was used as feedback to train the subjects to breathe consistently. The patients then used the feedback system throughout the study to insure reproducible flow rate and tidal volumes. The breathing maneuvers were performed in sequential phases of 10 breaths through the tube followed by a 30 second rest period, followed by the next randomly chosen tube size. During the breathing study the saturation, pulse rate, and PPG were recorded continuously from the nasal alar and the respiratory flow rates and volume were recorded using the $CO_2SMO$ Plus device.

Upon completion of the breathing maneuvers, the mouthpiece was removed and the donation/HD began. Upon completion of donation/HD, the breathing maneuvers were repeated. The order of the three resistance levels was again randomized. Upon completion of the second set of breathing maneuvers, the pulse oximeter probe was removed and data collection ceased. Subjects were paid for participation.

Data Analysis

Figure 6:
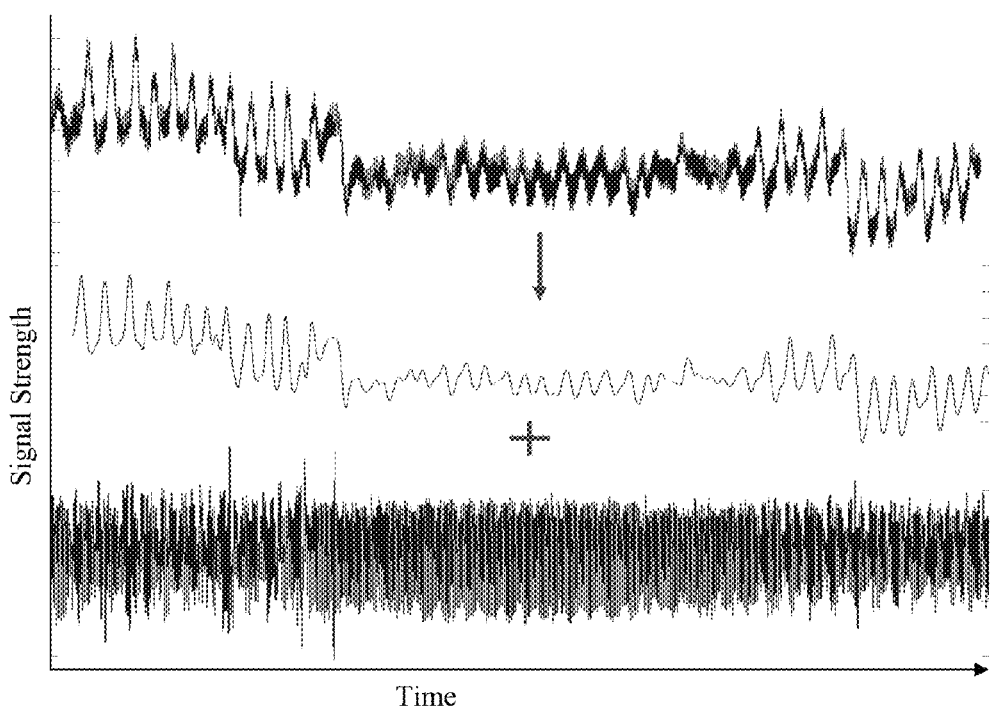
FIG. 6 shows a line graph representing the frequency separation of the raw PPG signal (top) into the VCC (middle) and PCC (bottom) using a standard Butterworth filter.
Figure 7:
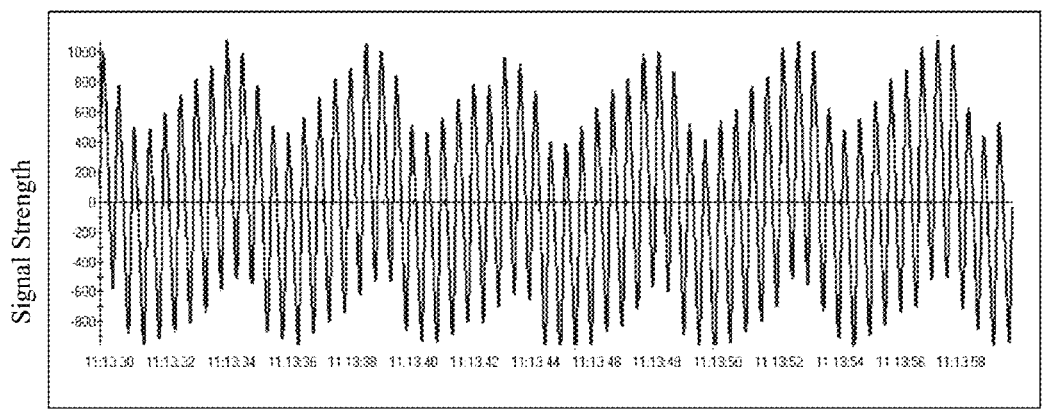
FIG. 7 shows expanded view of a PPG tracing demonstrating the respiratory pattern and rapid cardiac component (PCC)
Figure 8A:
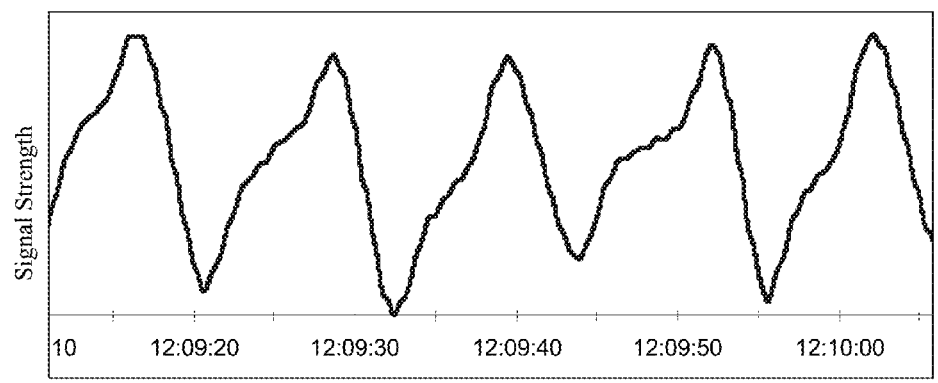
FIG. 8a shows an expanded view of a PPG tracing filtered so as to demonstrate the venouse capacitance component (VCC).
Figure 8B:
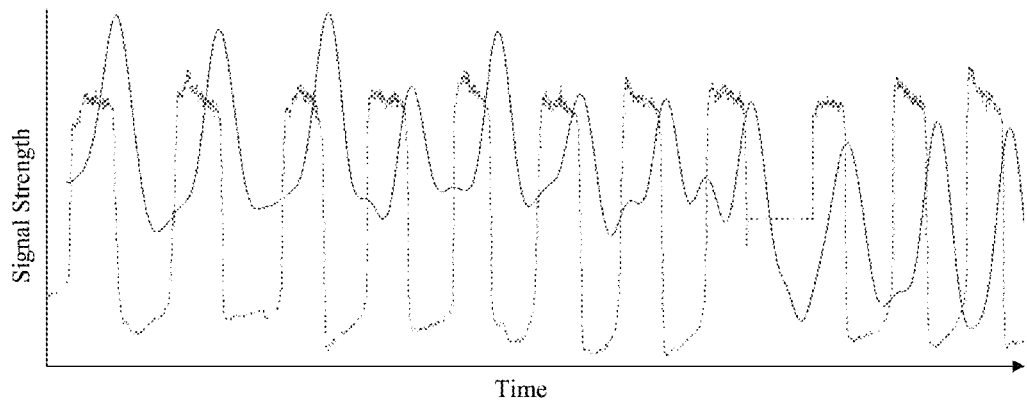
FIG. 8b shows a pattern of the PCC PPG plotted with the respiratory flow (dashed line).

For each blood donor and HD subject there were six raw data sets corresponding to the three airway resistances before and after their respective procedures. First, a standard high and low pass Butterworth filter was used to separate the data into the two (PCC and VCC) frequencies (FIG. 6). FIGS. 7 and 8 demonstrate examples of the effectiveness of the frequency separation. Next individual breaths were identified using the flow data recorded from the $CO_2SMO$ Plus device: each breath was defined as the interval between peaks of inspiratory flow. Utilizing the breath, low and high frequency data we were then able to calculate the three outcome variables of interest. The primary measure of interest was the fluctuation in the VCC caused by respirations, which we anticipated were going to be exaggerated with the incremental airway resistance. We defined $VCC_{var}$ as the maximum VCC value minus the minimum VCC value of each breath and calculated it for all breaths. The other two outcome variables were based on the PCC and its frequency corresponding to the heart rate. FIG. 6 demonstrates an example of a PCC wave tracing having approximately eight heart beats during one breath. Corresponding to each cardiac cycle's effect on the alar vasculature distention, the sensor photodiode has maximum and minimal signal strength values; the difference between those values thereby represents the waveform's amplitude, and we explored whether it varied with breathing. We defined $PCC_{amp}Diff$ as the difference between the largest and the smallest amplitude during each breath. We felt this would correlate with the stroke volume fluctuation during the respiratory cycle and might potentially be influenced by concurrent changes in vascular tone in the carotid vessels. We also calculated an average value of the waveform amplitude ($PCC_{amp}Mean$) over the course of the entire breath cycle. This was normalized by adjusting for heart rate, and was thought to reflect the average carotid component of the cardiac output over a breath cycle. Notably, these two PCC variables could only be computed for the lowest level of airway resistance. Breathing through the two smaller endotracheal tubes caused very large respiratory low frequency variations in the PPG. These baseline tracing variations were several orders of magnitude larger than the PCC and distorted the PCC frequency.

Prior to calculating the three outcome variables, the raw data were reviewed so as to identify possible technical sources of error. Considering that there was an enormous amount of data which corresponded to all the heart beats over long breathing intervals, there were very few artifacts. Less than 5% of the data had to be eliminated for the three causes of obvious artifact: complete loss respiratory flow measurements during the periodic $CO_2SMO$ Plus device's purging of gases; cardiac arrhythmias (i.e. occasional extra systoles); and probe movement interfering with the light signal.

Statistical Analysis:

The data for the ten breaths at each level of resistance were averaged so as to yield a single $VCC_{var}$ value for each level of resistance for each subject. There were corresponding averaged values for the $PCC_{amp}Diff$ and $PCC_{amp}Mean$ at just the low level of resistance, as described above. The data were analyzed for changes in these parameters following the fluid removal by either blood donation or dialysis. The Wilcoxon signed-rank test was used for all comparisons since the data were not normally distributed, as determined the Kolmogorov-Smirnov test with Lilliefors correction Results The probes were comfortable to the subjects, produced reliable signals, and the waveforms permitted analysis by our algorithms without problems due to signal artifact (as described above). There were no statistical differences in the respiratory flow rates or tidal volumes before and after the procedures, which could have potentially confound the results.

The blood donors were 34.8±14.4 (standard deviation) years old (range 19 to 65 years), and 7 (35%) were male. They were successfully phlebotomized approximately 500 ml of whole blood, and there were no statistically significant changes in their blood pressures or heart rates. The dialysis patients were characterized by having an age of 48.6±12.7 years (range 26 to 80 years), 10 (50%) were male, and underwent 2843±982 ml of ultrafiltration using an F160 polysulfone hemofilter (Fresenius Medical Care, Inc., Lexington, Mass.) during three or four hour hemodialysis treatments at a blood flow of approximately 450 ml/min. Although all were felt to be clinically hemodynamically stable and asymptomatic during their treatments, there was a significant increase in pulse rate (75±9 to 81±12 beats/min, p<0.01) and decrease in systolic (132±14 to 115±19 mm Hg, p<0.001) and diastolic (72±13 to 64±12 mm Hg, p<0.01) blood pressures.

Figure 9:
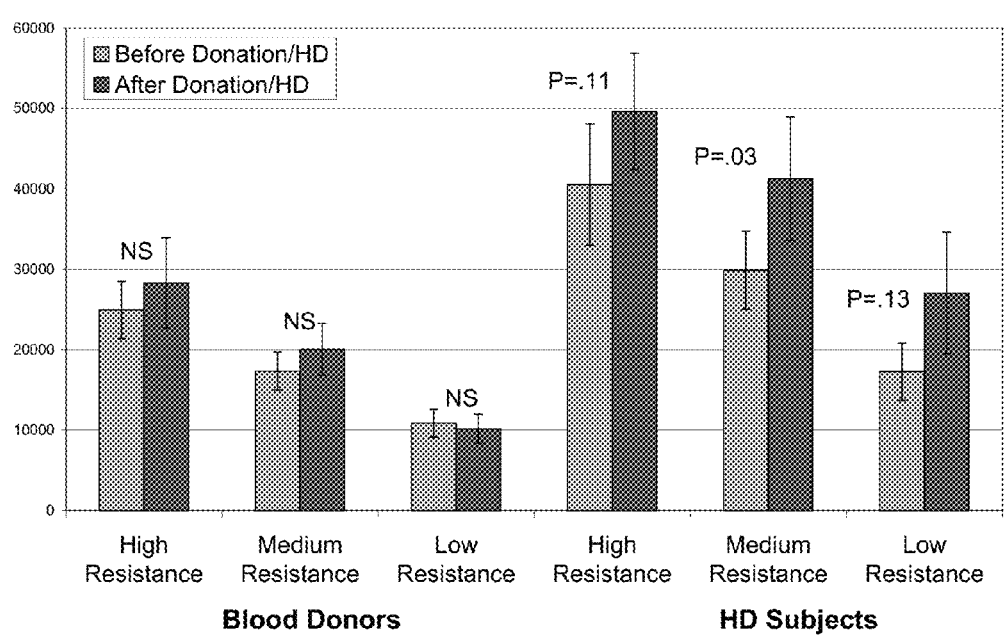
FIG. 9 shows a bar graph representing VCC swings for blood donor and HD subjects and the corresponding P-values. Error bars indicate standard error of measure. NS=not significant.

Concerning the respiratory VCC, (FIG. 9), there was no significant change after blood donation (p=0.82, 0.50, 0.91) at any level of airway resistance. After volume removal with hemodialysis, however, the $VCC_{var}$ increased significantly (p=0.03 with the medium resistance) or trended towards significance with all the airways (p=0.11 and 0.13). There was no significant correlation between the $VCC_{var}$ and either the absolute volume ultrafiltered nor the fluid removed as a percentage of total body weight.

Figure 10:
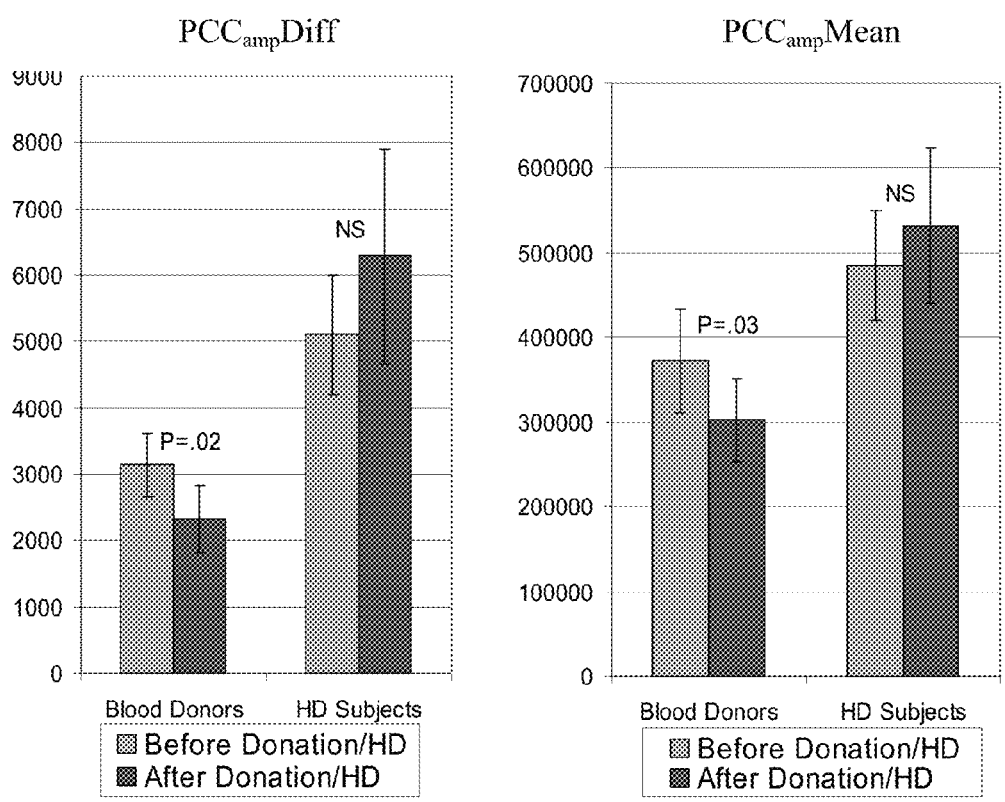
FIG. 10 shows a bar graph representing PCC AMPDiff and PCC AMPMean for blood donor and HD subjects and the corresponding P-values. Error bars indicate standard error of measure. NS=not significant.

Conversely, the blood donors had significant changes in the PCC parameters that were not observed in the dialysis patients (FIG. 10). Both the $PCC_{amp}Diff$ and $PCC_{amp}Mean$ decreased significantly (p≤0.03) after donation. There was no statistically significant relationship between either of these parameters and the percent of total blood volume (estimated using Allen's formula [11]) undergoing phlebotomy.

Discussion

This new noninvasive PPG method can detect altered respiration-associated carotid circulation during ultrafiltration. With blood donation there is dampening of pulsatile vessel distention, consistent with increased vascular tone. That compensatory mechanism was impaired in dialysis patients and helps explain their instability with fluid removal.

The inventors believe that the integrity of the various vascular and neurohumoral mechanisms to compensate for hypovolemia is a key factor in whether devices that monitor hemoconcentration can accurately predict clinical outcomes. Indeed volume removal using a carefully constructed algorithm did not lead to fewer adverse events, and in fact there were more deleterious outcomes and hospitalizations (Reddan D N, Szczech L A, Hasselblad V, Lowrie E G, Lindsay R M, Himmelfarb J, Toto R D, Stivelman J, Winchester J F, Zillman L A, Califf R M, Owen W F Jr. Intradialytic Blood Volume Monitoring in Ambulatory Hemodialysis patients: A Randomized Trial. Journal of the American Society of Nephrology. 2005; 16:2162-9). To date, there has not been a simple noninvasive technology that can continuously and reliably quantify the effect of fluid loss on circulation parameters. Several previous researchers have explored the possibility of using photoplethysmography (derived non-invasively using a pulse oximeter) to monitor the cardiovascular responses to fluid loss and volume status. In 1987, Partridge (Partridge, B. Use of Pulse Oximetry as a Noninvasive Indicator of Intravascular Volume Status. Journal of Clinical Monitoring. 1987; 3:263-268) discussed a possible correlation of PPG findings with intra-arterial blood pressure patterns induced by hypovolemia. Similarly, Shamir et al. (Shamir, M., Eidelman, L. A., Floman, Y., Kaplan, L. and Pizov, R. Pulse Oximetry Plethysmographic Waveform During Changes in Blood Volume. British Journal of Anaethesia. 1999; 2:178-81) reported an effect of a 10% blood volume phlebotomy and then reinfusion on PPG tracings. While very promising, prior studies such as these had a number of technologic limitations. Data analysis was limited by having only relatively crude printouts, as there was no automated collection that would permit microprocessor-based filters and algorithms for interpretation of the superimposed waveforms. More importantly only finger pulse oximeter probes were used, and that peripheral location yields a dampened PPG signal that is rather insensitive to physiologic events. Unfortunately when measurements are made with more tolerable superficial or indirect contact, the PPG becomes extremely susceptible to movement artifact and light interference. For these reasons we chose to instead utilize the nasal alar: it is fed by the same branches of the internal and external carotid arteries as the septum and is protected by a layer of epidermis. This allows for a probe that can be applied comfortably and with snug pressure to reduce artifacts.

The current investigation demonstrates the feasibility of designing and constructing a nasal alar PPG probe that yields a stable signal amenable to automated analysis. Algorithms were developed that calculate a number of respiratory and cardiovascular parameters that provide insight into the physiology of fluid losses and the compensatory mechanisms that are deranged in certain patient populations. Even in this preliminary study with modest ultrafiltration during dialysis, there was demonstrable effect of fluid removal on respiration-associated changes in the PPG (the $VCC_{var}$, FIG. 3). Not clear is whether that surrogate marker of carotid circulation would have decreased as much in healthy volunteers if they had comparably large phlebotomy volumes. It is possible that normal compensatory mechanisms decrease venous capacitance in response to hypovolemia, and thereby prevent or blunt the increase in $VCC_{var}$ detected in the dialysis patients. The tone of the smooth muscles in the venous capacitance system is influenced by both sympathetic and parasympathetic pathways, and these mechanisms are impaired in the end-stage renal disease population. The lack of significant $VCC_{var}$ findings in the blood donors may be due to the small volume of blood removal, although theoretically it could also be due to normal compensatory decreases in venous capacitance. In this regard the significant changes in the PCC parameters, discussed below, are consistent with there having been a physiologic effect from the blood donation. In addition, the inventors utilized various sizes of airway resistance to exaggerate alterations in thoracic pressures for the purposes of developing this new technology.

The discrepant findings in the PCC parameters between the two subject populations are consistent with uremic patients who have lost their compensatory mechanisms to maintain carotid flow homeostasis in the setting of hypovolemia. We suggest that the dampening of the magnitude of vessel pulsations (reflected in significant decreases in both the $PCC_{amp}$-Diff and $PCC_{amp}$Mean) after blood donation is due to the normal response of increased vascular tone. The loss of that response in dialysis patients would explain the unchanged PCC values, and would explain this population's susceptibility to hypotension with even modest fluid losses. According to another embodiment, the invention pertains to a method of determining a patients susceptibility to hypotension and/or complications during RRT by evaluating the patients compensatory mechanisms.

It should be understood that the examples and embodiments described herein are for illustrative purposes only and that various modifications or changes in light thereof will be suggested to persons skilled in the art and are to be included within the spirit and purview of this application and the scope of the appended claims. The full disclosures of all references are incorporated herein to the extent not inconsistent with the teachings herein.

What is claimed is:

1. A device for monitoring and controlling renal replacement therapy, said device comprising
    a computer that communicates with at least one pulse oximeter/photoplethysmography probe, said computer comprising
    at least one processing module;
    a first computer-readable program code module that causes said computer to separate a signal stream from said at least one pulse oximeter/photoplethysmography probe into an isolated pulsatile cardiac component signal stream, an isolated venous capacitance component signal stream, or both;
    a second computer-readable program code module that causes said computer to analyze said isolated pulsatile cardiac component signal stream and/or said isolated venous capacitance component signal stream to determine changes in blood flow, blood volume status, or both; and
    a third computer-readable program code module that causes said computer to adjust said renal replacement therapy, without need for user input, in response to a change in said isolated pulsatile cardiac component signal stream and/or said isolated venous capacitance component signal stream, whereby said therapy is adjusted until said isolated pulsatile cardiac component signal stream and/or said isolated venous capacitance component signal stream is modulated to a target level.

2. The device of claim 1, further comprising a display screen effective to display information to a user of said device.

3. The device of claim 1, wherein said third computer-readable program code module adjusts said renal replacement therapy in response to a change in an area under the curve (AUC) of said isolated pulsatile cardiac component signal stream and/or an AUC of said isolated venous capacitance component signal stream.

4. The device of claim 1, wherein said third computer-readable program code module adjusts said therapy in response to a change in an amplitude of said isolated pulsatile cardiac component signal stream and/or an amplitude of said isolated venous capacitance component signal stream.

5. The device of claim 1, wherein adjusting said therapy comprises increasing or decreasing a fluid removal rate.

6. The device of claim 5, wherein adjusting said therapy comprises decreasing said fluid removal rate.

7. The device of claim 5, wherein said fluid removal rate is an ultrafiltration rate.

* * * * *